United States Patent [19]

Davis

[11] Patent Number: 5,049,135
[45] Date of Patent: Sep. 17, 1991

[54] MEDICAL LAVAGE APPARATUS

[75] Inventor: Richard C. Davis, Palm Harbor, Fla.

[73] Assignee: Code Blue Medical Corporation, Clearwater, Fla.

[21] Appl. No.: 584,141

[22] Filed: Sep. 18, 1990

[51] Int. Cl.$^5$ ............................................. A61M 5/00
[52] U.S. Cl. .................................. 604/181; 604/187; 604/191; 604/218; 604/220
[58] Field of Search ............... 604/181, 187, 191, 218, 604/220, 207

[56] References Cited

U.S. PATENT DOCUMENTS

| | | |
|---|---|---|
| 13,975 | 12/1855 | Buhler . |
| 386,603 | 7/1888 | Parsons . |
| 1,496,126 | 6/1924 | Livingstone . |
| 3,159,312 | 12/1964 | Van Sciver, II ..................... 222/137 |
| 3,398,743 | 8/1968 | Shalit . |
| 3,450,134 | 6/1969 | Willgerodt . |
| 3,818,907 | 6/1974 | Walton . |
| 3,828,980 | 8/1974 | Creighton et al. ..................... 222/137 |
| 4,044,757 | 8/1977 | McWhorter et al. ........... 604/220 X |
| 4,046,166 | 9/1977 | Bender ........................... 137/625.48 |
| 4,054,137 | 10/1977 | Lee et al. . |
| 4,260,077 | 4/1981 | Schroeder ........................... 222/137 |
| 4,662,868 | 5/1987 | Cambio, Jr. ........................... 604/32 |
| 4,857,056 | 8/1989 | Talonn ........................... 604/191 X |
| 4,883,471 | 11/1989 | Braginetz et al. ............. 604/218 X |
| 4,979,942 | 12/1990 | Wolf et al. ........................... 604/191 |

Primary Examiner—John D. Yasko
Attorney, Agent, or Firm—Griffin, Branigan & Butler

[57] ABSTRACT

An improved medical lavage apparatus (10) includes guide/lock/stop tabs (122) which are inserted through a medical lavage syringe housing (20) into irrigation and aspiration bores (30, 34) thereof for engaging longitudinal ribs (68a–d, 69a–d) of irrigation and aspiration plungers (24, 26) to prevent their rotation and a circumferential latch rib 134a of the aspiration plunger for locking the aspiration plunger in an inserted position. The tabs also contact end circumferential ribs 70' of the plungers for providing stops to prevent the plungers from being removed from their respective bores. The tabs comprise two legs (126) which straddle the longitudinal ribs, with a longitudinal rib 68a of the aspiration plunger having a notch (140) at the tab in the aspiration bore to allow rotation of the aspiration plunger when it is in the inserted position for engaging the legs with the circumferential latch rib.

29 Claims, 2 Drawing Sheets

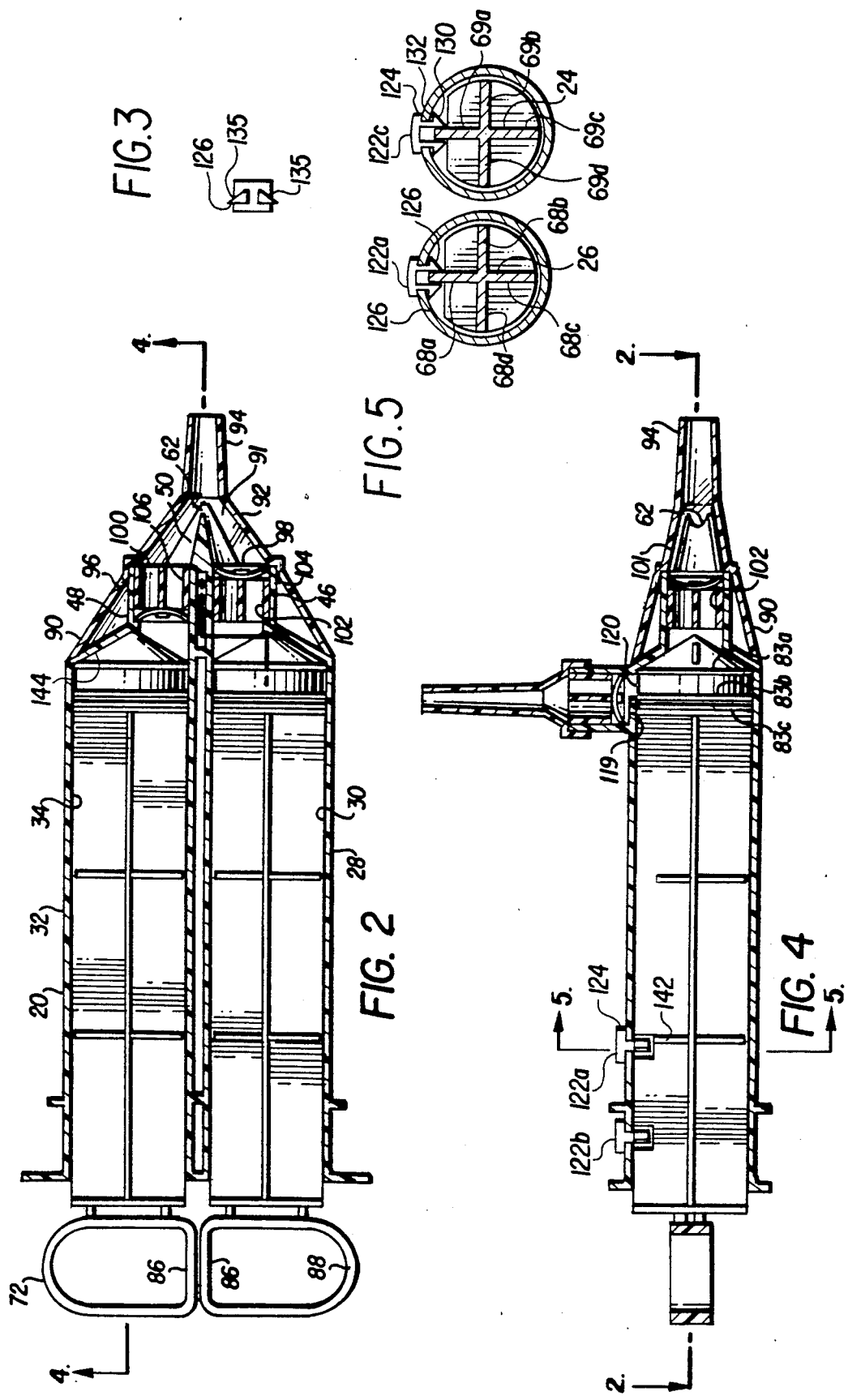

MEDICAL LAVAGE APPARATUS

BACKGROUND OF THE INVENTION

This invention relates broadly to the art of medical lavage devices and particularly to those which can be used for quickly exchanging fluids of body cavities.

This invention can be used with medical lavage apparatus of the type disclosed in U.S. Pat. Nos. 4,872,866 and 4,842,581 to Davis.

U.S. Pat. Nos. 4,872,866 and 4,842,581 to Davis describe medical lavage apparatus comprising parallel irrigation and aspiration cylinders communicating with a common exchange tube. The irrigation cylinder includes an inlet port and the aspiration cylinder includes an outlet port through which fluid from a supply container is pumped into and out of the body cavity as irrigation and aspiration plungers are moved in their respective cylinders. These patents disclose an anti-venturi septum and various valves which channel fluid flow from a supply container into the body cavity and out of the body cavity through the outlet port to a waste container. These patents also disclose loop handles having adjacent, relatively-straight, parallel, sides positioned close to each other to allow a user to grip and operate both the irrigation and aspiration plungers at the same time as well as individually.

Although the medical lavage syringe device of these patents has proven to be quite beneficial, several improvements would be helpful to improve its performance over a wider range of operation. Under normal circumstances, where an evacuation fluid is moderately clean, simultaneous operation of the irrigation and aspiration plungers directs evacuation fluid as described above. However, should the exchange tube, or a tube attached to the exchange tube extending into the cavity to be evacuated, become clogged with debris, simultaneous operation of the plungers can cause fluid to travel directly from the inlet port of the irrigation cylinder to the outlet port of the aspiration cylinder without going into the cavity to be evacuated. Thus, it is an object of this invention, to provide a medical lavage syringe having irrigation aspiration plungers which can be operated in a foolproof manner to assure that irrigation fluid passes through a cavity to be evacuated.

A feature of the medical lavage syringe device of U.S. Pat. Nos. 4,872,866 and 4,842,581 to Davis is that when the aspiration plunger thereof is fully inserted in its aspiration cylinder its seal covers the outlet port so that the irrigation plunger can be operated to pump fluid from the supply container into the cavity to be evacuated without fear of this fluid passing directly to the outlet port. However, when one fully seats the aspiration plunger and then operates the irrigation plunger against a debris-filled exchange tube, fluid pressure tends to move the aspiration plunger away from the fully seated position, thereby again uncovering the outlet port and allowing fluid to by-pass directly from the inlet port to the outlet port without going into the cavity to be irrigated. It is therefore an object of this invention, to provide a medical lavage syringe device of the type described in which an irrigation plunger thereof can be independently operated with assurance that fresh evacuation fluid is pumped into a cavity to be evacuated.

The loop handles of the above described patents can only be gripped in a manner intended for operating both the irrigation and the aspiration plungers simultaneously when they are aligned with one another. However, it has been found, that the plungers tend to rotate easily in their respective cylinders so that when the plungers are operated individually, the handles tend to come out of alignment. Thus, it is another object of this invention, to provide a medical lavage syringe device of the type described in which plungers, and handles therefor, remain in a fixed rotational orientation while they are being driven.

Yet another difficulty with the medical lavage syringe device described in the above cited patents is that when the plungers thereof are being operated, they can be easily inadvertently pulled from their respective cylinders, and/or driven from their respective cylinders by fluid pressure. If the plungers come out of the cylinders, this can contaminate clean areas and can be quite messy. Further, it can be time consuming and quite awkward for an operator to have to reinsert the plungers. Thus, it is another object of this invention to provide a medical lavage syringe device, of the type described, in which the plungers are not allowed to inadvertently leave their respective cylinders.

SUMMARY OF THE INVENTION

According to principles of this invention, a medical lavage syringe device includes a housing having tabs therefor which engage longitudinal followers on irrigation and aspiration plungers for causing these plungers to stay in a particular rotational orientation during their operation. The aspiration plunger includes a latching surface which engages a tab surface when the aspiration plunger is rotated in an inserted position for locking the aspiration plunger in the inserted position. The plungers include stop surfaces which contact tab surfaces for preventing the plungers from leaving their respective cylinders. In the preferred embodiment, a single tab can serve as a guide, lock and stop tab of an aspiration cylinder and another single tab can serve as a guide, and stop tab of an irrigation cylinder.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 2 is a top, partially cross-sectional, view of the lavage apparatus of FIG. 1 taken on line 2—2 in FIG. 4;

FIG. 3 is a bottom view of a tab which is part of the lavage syringe device of FIG. 1;

FIG. 4 is a side, partially sectional, view of the apparatus of FIG. 2, taken on line 4—4; and FIG. 5 is a segmented, partially cross-sectional, view taken on line 5—5 of FIG. 4.

DESCRIPTION OF THE PREFERRED EMBODIMENT

Figure 1:
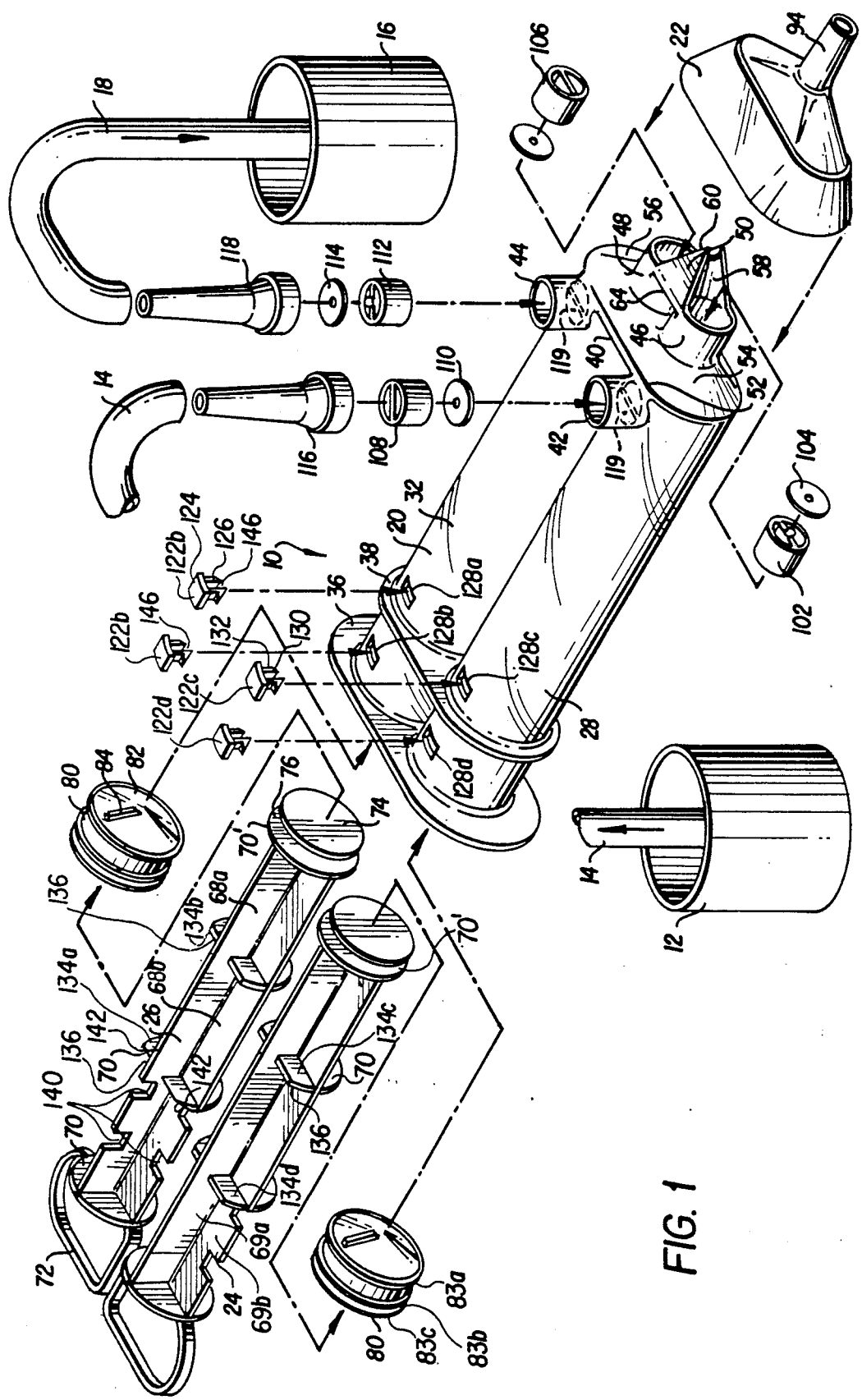
FIG. 1 is an isometric exploded, view of a medical lavage syringe device of this invention and further including waste and source containers and tubes to be used with the lavage device.

A lavage apparatus 10 is shown in FIG. 1 for use with a supply container 12, a supply tube 14, a waste container 16 and a waste tube 18.

The lavage apparatus 10 comprises a rigid housing 20, a common exchange tube 22, an irrigation plunger 24, an aspiration plunger 26, and a system of seals and valves associated therewith.

Looking first at the rigid housing 20, this housing is molded as one piece of a medical grade, translucent polycarbonate (LEXAN, a trademark of General Electric) plastic. The rigid housing 20 has an irrigation cylinder 28 defining an irrigation-cylinder bore 30, an aspiration cylinder 32 defining an aspiration-cylinder bore 34, first and second supporting flanges 36 and 38 holding together first ends of the irrigation and aspiration cylinders 28 and 32, a third flange 40 holding together second ends of the irrigation and aspiration cylinders 28 and 32, an inlet port 42 located near a second end of the irrigation cylinder 28 an outlet port 44 located near a second end of the aspiration cylinder 32, an irrigation check-valve cylinder 46 located at the end of the irrigation cylinder 28 and an aspiration check-valve cylinder 48 located at the second end of the aspiration cylinder 32, and an anti-venturi septum 50 joining the second ends of the irrigation and aspiration check-valve cylinders 46 and 48. As can be seen in FIG. 1, the first, second, and third flanges 36, 38, and 40 hold the irrigation cylinder 28 and the aspiration cylinder 32 in a side-by-side, parallel, relationship. The bores 30 and 34 of the respective irrigation and aspiration cylinders 28 and 32 are the same size, each providing approximately 125 cc's in actual stroke volume when the plungers are withdrawn to stops thereof.

The inlet and outlet ports 42 and 44 are close to the second ends 52 of the irrigation and aspiration cylinders 28 and 32 in the form of small, equal sized, valve cylinders extending perpendicular to axes of the irrigation and aspiration cylinders 28 and 32. This increases the turbulence of fluid flow allowing for increased mixing and dissolution of aspirated contents thereby reducing valve clogging.

It can be seen in FIG. 1 that the equal sized irrigation and aspiration check-valve cylinders 46 and 48 are connected to their respective irrigation and aspiration cylinders 28 and 32 by tapered bonnets 54 and 56, respectively so as to be close to, and parallel with one another. In this respect, the circumference of the check-valve cylinders 46 and 48 is about half that of the irrigation and aspiration cylinders 28 and 32 and their axes are offset from those of the irrigation and aspiration cylinders 28 and 32 so that the irrigation and aspiration check-valve cylinders 46 and 48 are close to one another with their bores aligned with the irrigation and aspiration cylinder bores 30 and 34.

The septum 50 has an irrigation baffle 58 and an aspiration baffle 60, each of which is semi-circular in cross-sectional shape. These baffles intersect at an outer tip 62 which forms a U-shaped line. In this regard, the septum baffles 58 and 60 are only positioned on the inside sides of the check valve cylinders 46 and 48 so as to guide fluid from and to the check-valve cylinders 46 and 48. A fourth flange 64 interconnects the outer ends of the check-valve cylinders 46 and 48 and forms an oval with these outer ends.

The plungers 24 and 26 are molded to be identical, each having shafts comprised of crossed longitudinal ribs 69a-d (for the irrigation plunger) and 68a-d (for the aspiration plunger) supported circumferentially by circumferential ribs 70. Also molded integral therewith are finger-engaging portions 72 and seal mounting ribs 74. Seal-mounting ribs 74 are separated from stop or last circumferential ribs 70' by a space 76 into which internally directed ribs (not shown) of seals 80 are inserted for holding the seals thereon. Each seal 80 has a cone-shaped end 82 with small ridges 84 thereon. There are three cylinder-bore contacting rings 83a, b, and c on the outer surface thereof.

It should be noted from FIGS. 1 and 2 that the finger-engaging portions 72 of the plungers 24 and 26 are respectively turned so that they provide mirror images, one of the other. In this respect, the finger-engaging portions 72 are not geometrical, being flat at first sides 86 thereof and rounded at second sides 88 thereof. The reason for this is so that the first sides 86 can be as close together, between two adjacent fingers, as possible where it is desirable to operate the syringes simultaneously. Thus, although the plungers are not connected, these finger engaging portions are designed to allow easy use of one of the plungers or both as is desired. This allows one to "prime the pump", so to speak, with the irrigation half of the system upon beginning use of the lavage apparatus.

The common exchange tube 22 is oblong, or oval, in cross section to thereby form an oblong chamber 91 in which fluid flows to and from the irrigation and aspiration cylinders 28 and 32. The common exchange tube 22 includes an apron portion 90, a manifold portion 92, a common nozzle portion 94, and an attachment ridge 96. The attachment ridge 96 is of a size to sealingly fit about the side-by-side irrigation and aspiration check-valve cylinders 46 and 48 and the fourth flange 64 which joins them. In use, these members are held together by sonic welding or by an adhesive. The apron portion 90 makes the entire apparatus more streamlined in appearance and for handling, however, it is not necessary for operation of the lavage apparatus.

The manifold portion 92 encloses and seals with outer ends 98 and 100 of the irrigation and aspiration check-valve cylinders 46 and 48 as well as the septum 50, as can be seen in FIG. 2, so that all material flowing to and from the outer ends 98 and 100 are guided by the septum 50 and the manifold portion 92. Similarly, all fluids flowing to and from the manifold portion 92 flow through the common nozzle 94. It should be noted that the septum 50 is so arranged and designed that fluid streams flowing from the irrigation check-valve cylinder 46 will be directed into the nozzle 94 and fluid flowing from the nozzle 94 will be directed to the aspiration check-valve cylinder 48 without restriction and without causing undue turbulence. In this manner, such fluid streams are not caused to cross mix. The U-shaped outer tip line 62 particularly aids in avoiding undue cross mixing by not causing a venturi restriction to create a negative pressure in the manifold portion 92 which improperly opens a check-valve. Sidewalls of the septum 50 press against interior surfaces of the manifold at 101 to create a seal therebetween.

With regard to the check valves, an irrigation check valve 102 has a cylinder outer wall with a cross-wall carrying a resilient membrane 104 thereon which flexes open when pressure is exerted from the irrigation-cylinder bore 30 toward the nozzle 94 but closes when pressure is exerted in the opposite direction. An aspiration check valve 106 in the aspiration check-valve cylinder 48 operates in a similar but opposite manner. An inlet check valve 108, with an attached membrane 110, allows fluid to flow into the irrigation cylinder 28, but does not allow flow from the irrigation cylinder 28. Similarly, an outlet check-valve 112 allows fluid flow from the aspiration cylinder 32, however, it does not allow flow therein. Funnel-like inlet and outlet adaptors 116 and 118 are respectively attached to the inlet port 42 and the outlet port 44.

Regarding the inlet and outlet ports 42 and 44, these are each restricted by a shelf 119 (FIG. 4) which makes an actual port opening 120 have an elongated (semicircular) shape and have the same cross-sectional area as the bore of the nozzle 94. The approximate matching of these sizes balances pressures within the system so as to avoid improper opening of the check-valves during operation and thereby avoid cross mixing of contaminated and pure fluids. The shelves 119 have the additional purpose of creating elongated port openings 120 which allow the openings 120 to be fully sealed by the relatively-close-together contacting rings 83a, b, and c when the respective plungers 24 and 26 are fully depressed, as shown in FIG. 4. Still further, the shelf 119 at the aspiration outlet port 44 tends to break up solids which might otherwise jam the membrane 114. Finally, the shelves 119 allow rather large membrane type check-valves to be used with necessarily smaller valve openings 120. These larger check valves are not as vulnerable to jamming as smaller ones.

All of the various rigid components of this invention can be constructed of a rigid hard resinous plastic such as polycarbonate (LEXAN).

In operation of the lavage apparatus of this invention described to this point, the rigid housing 20, the two plungers 24 and 26, the common exchange tube 22, and the various check valve cylinders 102, 106, 108, and 112 and the inlet and outlet adaptors 116 and 118 are molded of hard resinous plastic. In this respect, all of the check-valves are the same size so as not to require more than one mold for these elements. The plunger seal 80 and the various check-valve membranes are molded, or purchased off-the-shelf. The plunger seals 80 are attached to plungers 24 and 26 and the various check-valve membranes are attached to knobs on the check-valve cylinders 102, 106, 108, and 112. The check valve cylinders are then attached by press fitting or sonic welding in their respective positions to the rigid housing 20 as is depicted in the exploded view of FIG. 1. Thereafter, the attachment ridge 96 of the common exchange tube 22 is sealingly adhered to the irrigation and aspiration check valve cylinders 46 and 48 and the flange 64 which adjoins these two ridges. The various valves cannot be easily serviced, but that is not necessary since the lavage apparatus is designed to be a single use, disposable product.

To utilize the lavage apparatus 10 one places a lavage liquid in the supply container 12 which is joined via a supply tube 14 and the inlet adaptor 116 to the inlet port 42. The waste container 16 is similarly attached via tube 18 and outlet adaptor 118 to the outlet port 44. The lavage solution is to be instilled into a body cavity, left for a short length of time and then sucked out. A tube (not shown) is attached to the nozzle 94 of the common exchange tube 22 which is inserted through an opening in the human body into an organ to be lavaged. Where fluid from more than one irrigation cylinder 28 is to be inserted into the organ before any is aspirated, the aspiration plunger 26 is inserted fully into the aspiration cylinder 32 as is depicted in FIGS. 2 and 4. In this position, the aspiration plunger seal 80 completely seals the opening 120 of the outlet port 44. Thus, while the aspiration plunger 26 is left in this position, no fluid can flow through the outlet port 44. With the aspiration plunger 26 so situated, the irrigation plunger 24 is pulled outwardly to cause a vacuum in the irrigation cylinder 28. This vacuum respectfully opens the membrane 110 of the inlet check-valve 108 and closes the membrane 104 of the irrigation check-valve 102. Thus, fluid is sucked from the supply container 12 into the irrigation cylinder 28. Thereafter, the irrigation plunger 24 is driven into the irrigation cylinder 28 which closes the inlet check valve 108, opens the irrigation check valve 102, and drives fluid out of the irrigation cylinder 28 into the manifold portion 92 of the common exchange tube 22 and out the nozzle 94 of the common exchange tube 22. In this respect, the irrigation baffle 58 of the septum 50 guides this fluid to ensure that it enters the nozzle 94 rather than being driven through the aspiration check-valve cylinder 48 to open the aspiration check-valve 106 and thereby drive the plunger 26 from its blocking position. The irrigator plunger 24 is moved in and out until the body cavity has the right amount of fluid in it.

After the irrigation fluid has been left in the body organ for a period of time, the irrigation plunger 24 is driven fully into the irrigation cylinder 28 so that seal 80 covers the openings 120 of the inlet port 42 thereby not allowing flow of fluid through this port. Now the aspiration plunger is pulled out and pushed in, thereby sucking contaminated fluid from the body organ through the nozzle 94, and the aspiration check-valve cylinder 48, into the aspiration cylinder 32, driving the contaminated waste fluid out of the outlet port 44 into the waste container.

Ordinarily, most body organs requiring lavage will be of such a size as to hold multiple loads of the irrigation cylinder 28, with the skill of an operator protecting against over distension of a cavity. Once the appropriate amount of irrigant is instilled, the irrigation and aspiration plungers 24 and 26 will be gripped together and moved in and out simultaneously thereby maintaining a constant steady-state volume of fluid flow in the organ. On the out strokes the irrigation cylinder 28 will be loaded with fresh fluid from the supply container 12 and the aspiration cylinder 32 will be loaded with contaminated waste from the organ. On the in strokes the fresh fluid in the irrigation cylinder 28 will be forced into the organ and the contaminated waste fluid in the aspiration cylinder 32 will be forced into the waste container 16. During these strokes, since the openings 120 of the inlet and outlet ports 42 and 44 have the same cross-sectional size as the internal bore of the nozzle 94, the pressures applied at each of these by the equal size plungers 24 and 26 are approximately equal, there being only a small drop across each of the various valves to cause them to act as check valves in the appropriate directions. Similarly, the shape of the U-shaped outer tip line 62 of the anti-venturi septum 50 does not cause undue venturi or eddy effects which create undue changes in pressure at the nozzle 94 to improperly open the irrigation and aspiration check valves 102 and 106 to cause a mixing.

The lavage apparatus described to this point is basically the same device as was described in U.S. Pat. Nos.

4,842,581 and 4,872,866 to Davis. This basic structure is considerably improved by the use of guide/lock/stop tabs 122a, b, c and d depicted in FIG. 1. Each of these tabs 122a-d comprises a relatively thin base plate 124 having spaced spring legs 126 extending from a bottom surface thereof. The base plate 124 is slightly rounded to the circular outer surface contours of the irrigation and aspiration cylinders 28 and 32. The irrigation and aspiration cylinders 28 and 32 each have tab openings 128a, b, c and d therein for receiving the spring legs 126 of the tabs. In this respect, the spring legs 126 include ramp surfaces 130 (FIG. 5) and shoulders 132 such that when the spring legs 126 of a tab are inserted through a tab opening 128, the ramp surfaces engage end edges of the tab opening 128 forcing the spring legs 126 inwardly until the shoulders 132 are inside a cylinder bore. When this happens, the spring legs 126 can spring outwardly so that the shoulders 132 engage housing walls thereby preventing the tabs 122 from being removed from the tab openings 128. Once the tabs 122a-d are mounted in their respective tab openings 128a-d, their legs project into the appropriate bore 30 or 34, as can be seen in FIGS. 4 and 5. Another feature of the tab legs 126 is that when they are viewed from their bottom ends, as is depicted in FIG. 3, they have angled camming surfaces 133 whose purpose is described below.

The irrigation and aspiration plungers 24 and 26 are also constructed somewhat differently in this improvement. In this regard, intermediate circumferential ribs 134a, b, c and d for these plungers are notched at 136 adjacent a top longitudinal rib 68a and 69a. The longitudinal ribs 68a-d of the aspiration plunger differ from the longitudinal ribs 69a-d of the irrigation plunger 24 in that they include longitudinal notches 140 on outer edges thereof. Positions of the longitudinal notches 140 corresponding to axial, or longitudinal, positions of tab openings 128a and b in the aspiration cylinder 32.

Intermediate circumferential rib 134a is somewhat different than circumferential ribs 134b, c, and d in that it has latching cam surfaces 142 as can most clearly be seen in FIG. 4.

In further operation of the lavage apparatus 10, the apparatus is assembled by inserting the seals 80 and the stop, or last, circumferential ribs 70' of the plungers 24 and 26 into the open ends of the irrigation and aspiration cylinders 28 and 32 and shoving them past all of the tab openings 128a-d. The spring legs 126 of the guide/lock/stop tabs 122a-d are then inserted into their respective tab openings 128a-d until they are locked in place by the shoulders 132 on the spring legs 126. While the tabs 122 are being inserted into the tab openings 128, the irrigation and aspiration plungers 24 and 22 are held in rotative orientation as depicted in FIG. 1 with the loops of the finger engaging portions 72 aligned with one another, their straight sides 86 adjacent one another. In this position, the longitudinal ribs 68a and 69a are directed upwardly toward the middle of the tab openings 128 so that when the spring legs 126 are inserted into the tab openings 128a-d their legs straddle the respective longitudinal ribs 68a and 69a. For example, as can be seen in FIG. 5, the longitudinal rib 68a of the aspiration plunger 26 is positioned between the spring legs 126 of the guide/lock/stop tab 122a. In this position, the aspiration plunger 26 cannot normally be rotated because its longitudinal rib 168a engages the legs 126. However, if the aspiration plunger is fully inserted into the aspiration cylinder 32, the legs 126 then are aligned with the longitudinal notches 140 in the longitudinal ribs which allows clearance for the aspiration plunger 26 to be rotated. When the aspiration plunger 26 is rotated, one of the camming surfaces 135 of the spring legs 126 contacts one of the latching cam surfaces 142 of the intermediate circumferential rib 134a to thereby lock the aspiration plunger 26 in position. The irrigation plunger 24 can then be pulled in and out without fear of the aspiration plunger 26 moving from this fully inserted position in which its seal 80 covers the opening 120 of the outlet port 44. Thus, irrigating fluid cannot be transferred directly from the irrigation cylinder 28 through the outlet port 44, but rather, when the irrigation plunger 24 is worked, evacuation fluid is driven through the common exchange tube 22 into a cavity to be evacuated.

It should also be understood that the guide/lock/stop tabs 122a and c also serve as stops inasmuch as their spring legs 126 contact end or stop circumferential ribs 70' of the irrigation and aspiration plungers 24 and 26 to prevent these plungers from being removed from their respective cylinders. In this regard, only the intermediate circumferential ribs 134a-d have circumferential notches 136 therein for allowing these intermediate ribs to pass longitudinally past the various tabs.

Thus, the improvements described herein maintain the rotational orientations of the irrigation and aspiration plungers 24 and 26 unless the aspiration plunger 26 is rotated to be locked in a fully inserted position in which a seal 80 covers the outlet port 44. It should be noted that the irrigation plunger 24 need not be locked inasmuch as when the aspiration plunger 26 is independently operated, the irrigation plunger 24 is sucked to a fully inserted position in which its seal 80 covers the inlet port 42.

It will also be appreciated by those of ordinary skill in the art that it is beneficial for the guide/lock/stop tabs 122 to prevent the irrigation and aspiration plungers 24 and 26 from being inadvertently removed from their respective cylinders.

Although the invention is shown with two guide/lock/stop tabs 122 in each of the irrigation and aspiration cylinders 28 and 32, only one such tab is necessary for proper operation. Two tabs, however, provide additional guiding support to ensure proper plunger orientation.

While the invention has been particularly shown and described with reference to a preferred embodiment, it will be understood by those skilled in the art that various changes in form and detail may be made therein without departing from the spirit and scope of the invention. For example, guide/lock/stop protrusions of the type created by the spring legs 126 could be created in other ways. Further, it would be possible to create such protrusions radially outwardly from the plungers into grooves in walls of the irrigation and aspiration cylinders.

The embodiments of the invention in which an exclusive property or privilege are claimed or defined are as follows:

1. A medical lavage syringe device for irrigating and aspirating a body cavity, said device comprising:
  a housing defining an elongated irrigation cylinder with an irrigation bore and an elongated aspiration cylinder with an aspiration bore, said irrigation and aspiration cylinder bores each being open and unconnected at first ends thereof, said housing further defining respectively an inlet port and an outlet port in said respective irrigation and aspiration cylinders intermediate said first and second ends thereof, said housing further including an exchange tube at second ends of said irrigation and aspiration cylinder bores leading to a common nozzle;

an irrigation plunger and an aspiration plunger having first ends for respectively fitting into said first open ends of said irrigation and aspiration cylinders and having sliding seals at said first ends thereof for making sealing, sliding contact with internal cylinder surfaces of said respective bores and including hand-engaging portions at second ends outside the cylinders for engaging a hand and thereby being moved into and out of their respective bores by said hand;

a system of check valves comprising an inlet check valve located at said inlet port for allowing the flow of fresh irrigation fluid into said inlet port but hindering the flow of fluid from said inlet port, an outlet check-valve located at said outlet port for allowing the flow of aspiration fluid from said outlet port but hindering the flow of fluid into said outlet port, an irrigation check-valve located at said irrigation bore between said inlet port and said common exchange tube for allowing flow of irrigation fluid from said irrigation bore into said common exchange tube but for hindering the flow of fluid from said common exchange tube into said irrigation bore and an aspiration check-valve located at said aspiration bore between said outlet port and said common exchange tube for allowing flow of irrigation fluid from said common exchange tube into said aspiration bore but hindering flow in the opposite direction;

wherein, motion of said irrigation plunger into and out of said irrigation bore causes fluid to flow from said inlet port to said common exchange tube while motion of said aspiration plunger into and out of said aspiration bore causes fluid to flow from said exchange tube to said outlet port; and wherein is further included a locking means for locking said aspiration plunger in an inserted position in said aspiration bore so that it cannot be forced out of said bore by pressure from said common exchange tube.

2. A medical lavage syringe device as in claim 1 wherein said outlet port is blocked from receiving material from said exchange tube when said aspiration plunger is in said inserted position.

3. A medical lavage syringe device as in claim 2 wherein said outlet port is located in a sidewall of said aspiration cylinder to be directed laterally away from an axis of elongation thereof and wherein said aspiration plunger is appropriately long and said outlet port is appropriately located such that when said aspiration plunger is fully inserted in said aspiration cylinder said sliding seal extends beyond said outlet port to be positioned between said exchange tube and said outlet port when said aspiration plunger is in said inserted position.

4. A medical lavage syringe device as in claim 3 wherein said sliding seal of said aspiration plunger is of such a size that those portions thereof normally making sliding contact with said internal cylinder surface of said aspiration bore is large enough to cover said outlet port and wherein said outlet port is located such that when said aspiration plunger is locked in said inserted position in said aspiration cylinder said sliding seal completely covers said outlet port to prevent the flow of fluid therethrough.

5. A medical lavage syringe device as in claim 1 wherein said locking means is a tab and wherein a portion of the said tab extends through said housing into said aspiration bore and wherein said aspiration plunger includes a latch means for engaging said portion of said tab extending into said aspiration bore for locking these two members together when said aspiration plunger is rotated in the inserted position.

6. A medical lavage syringe device as in claim 5 wherein said aspiration plunger is comprised of circumferential ribs, one of which forms said latch means.

7. A medical lavage syringe device as in claim 6 wherein said circumferential rib forming said latch means has a tapered camming surface for engaging said portion of said tab extending into said aspiration bore.

8. A medical lavage syringe device as in claim 7 wherein said portion of said tab extending into said aspiration bore includes a tapered camming surface for contacting said circumferential rib forming said latch means.

9. A medical lavage syringe device as in claim 5 wherein said portion of said tab extending into said aspiration bore includes a tapered camming surface for contacting a portion of said plunger when said plunger is rotated.

10. A medical lavage syringe device as in claim 5 wherein the portion of said tab extending into said aspiration bore makes sliding engagement with a longitudinal follower portion of said aspiration plunger to prevent rotation of said aspiration plunger unless said plunger is in said inserted position.

11. A medical lavage syringe device as in claim 10 wherein said aspiration plunger is comprised of a longitudinal rib which forms said longitudinal follower portion of said aspiration plunger.

12. A medical lavage syringe device as in claim 11 wherein said portion of said tab extending into said aspiration bore comprises two spaced feet which straddle said longitudinal rib.

13. A medical lavage syringe device as in claim 12 wherein said longitudinal rib has a notch therein positioned longitudinally at said tab when said aspiration plunger is in the inserted position.

14. A medical lavage syringe device as in claim 1 wherein said locking means is a tab extending into said aspiration bore, said aspiration plunger including a longitudinal follower for contacting said tab to prevent rotation of said aspiration plunger except when said aspiration plunger is in said inserted position, and a latch means for contacting said tab when said plunger is rotated in the inserted position.

15. A medical lavage syringe device as in claim 1 wherein is further included a guide means for preventing rotation of said aspiration plunger except when said aspiration plunger is in said inserted position.

16. A medical lavage syringe device for irrigating and aspirating a body cavity, said device comprising:
a housing defining an elongated irrigation cylinder with an irrigation bore and an elongated aspiration cylinder with an aspiration bore, said irrigation and aspiration cylinder bores each being open and unconnected at first ends thereof, said housing further defining respectively an inlet port and an outlet port in said respective irrigation and aspiration cylinders intermediate said first and second ends thereof, said housing further including an exchange tube at second ends of said irrigation and aspiration cylinder bores leading to a common nozzle;

an irrigation plunger and an aspiration plunger having first ends for respectively fitting into said first open ends of said irrigation and aspiration cylinders and having sliding seals at said first ends thereof for making sealing, sliding contact with internal cylinder surfaces of said respective bores and including hand-engaging portions at second ends outside the cylinders for engaging a hand and thereby being moved into and out of their respective bores by said hand;

a system of check valves comprising an inlet check valve located at said inlet port for allowing the flow of fresh irrigation fluid into said inlet port but hindering the flow of fluid from said inlet port, an outlet check-valve located at said outlet port for allowing the flow of aspiration fluid from said outlet port but hindering the flow of fluid into said outlet port, an irrigation check-valve located at said irrigation bore between said inlet port and said common exchange tube for allowing flow of irrigation fluid from said irrigation bore into said common exchange tube but for hindering the flow of fluid from said common exchange tube into said irrigation bore and an aspiration check-valve located at said aspiration bore between said outlet port and said common exchange tube for allowing flow of irrigation fluid from said common exchange tube into said aspiration bore but hindering flow in the opposite direction;

wherein, motion of said irrigation plunger into and out of said irrigation bore causes fluid to flow from said inlet port to said common exchange tube while motion of said aspiration plunger into and out of said aspiration bore causes fluid to flow from said exchange tube to said outlet port; and wherein said irrigation and aspiration plungers include longitudinal followers and wherein said housing includes a guide means for engaging said longitudinal followers for preventing rotation of said plungers as said plungers are moved in and out of their respective irrigation and aspiration cylinders.

17. A medical lavage syringe device as in claim 16 wherein said irrigation and aspiration plungers are each comprised of a longitudinal rib which forms said longitudinal follower portion and wherein said guide means includes tabs having portions thereof extending into said irrigation and aspiration bores.

18. A medical lavage syringe device as in claim 17 wherein said portions of said tabs extending into said irrigation and aspiration bores forms stops for engaging stops on said plungers for preventing said plungers from being removed from their respective bores.

19. A medical lavage syringe device as in claim 16 wherein said guide means extend into said irrigation and aspiration bores to form stops for engaging stops on said plungers for preventing said plungers from being removed from their respective bores.

20. A medical lavage syringe device as in claim 16 wherein said hand-engaging portions of said irrigation and aspiration plungers have loop configurations, said loops having adjacent, relatively-straight, parallel, sides positioned close to each other to allow a user to grip both hand engaging portions with his fingers being close together when said plungers are being guided by said guide means.

21. A medical lavage syringe device for irrigating and aspirating a body cavity, said device comprising:

a housing defining an elongated irrigation cylinder with an irrigation bore and an elongated aspiration cylinder with an aspiration bore, said irrigation and aspiration cylinder bores each being open and unconnected at first ends thereof, said housing further defining respectively an inlet port and an outlet port in said respective irrigation and aspiration cylinders intermediate said first and second ends thereof, said housing further including an exchange tube at second ends of said irrigation and aspiration cylinder bores leading to a common nozzle;

an irrigation plunger and an aspiration plunger having first ends for respectively fitting into said first open ends of said irrigation and aspiration cylinders and having sliding seals at said first ends thereof for making sealing, sliding contact with internal cylinder surfaces of said respective bores and including hand-engaging portions at second ends outside the cylinders for engaging a hand and thereby being moved into and out of their respective bores by said hand;

a system of check valves comprising an inlet check valve located at said inlet port for allowing the flow of fresh irrigation fluid into said inlet port but hindering the flow of fluid from said inlet port, an outlet check-valve located at said outlet port for allowing the flow of aspiration fluid from said outlet port but hindering the flow of fluid into said outlet port, an irrigation check-valve located at said irrigation bore between said inlet port and said common exchange tube for allowing flow of irrigation fluid from said irrigation bore into said common exchange tube but for hindering the flow of fluid from said common exchange tube into said irrigation bore and an aspiration check-valve located at said aspiration bore between said outlet port and said common exchange tube for allowing flow of irrigation fluid from said common exchange tube into said aspiration bore but hindering flow in the opposite direction;

wherein, motion of said irrigation plunger into and out of said irrigation bore causes fluid to flow from said inlet port to said common exchange tube while motion of said aspiration plunger into and out of said aspiration bore causes fluid to flow from said exchange tube to said outlet port; and wherein said housing includes a stop means for engaging stop surfaces on said irrigation and aspiration plungers for preventing said plungers from being removed from their respective bores.

22. A medical lavage syringe device as in claim 21 wherein said stop means are tabs which are inserted through walls of said housing such that portions thereof extend into said irrigation and aspiration bores.

23. A medical lavage syringe device as in claim 22 wherein said irrigation and aspiration plungers further include longitudinal followers which engage said tab portions extending into said bores to allow said irrigation and aspiration plungers to move longitudinally in said bores, but to prevent rotative movement thereof in said bores.

24. A medical lavage syringe device as in claim 23 wherein one of said irrigation and aspiration plungers includes a latch means for engaging said portion of said tab extending into the bore in which it is located when said plunger is rotated to thereby prevent said plunger from moving longitudinally in said bore.

25. A medical lavage syringe device as in claim 24 wherein said longitudinal follower means and said latch means are longitudinal and circumferentially positioned ribs.

26. A syringe including a cylinder housing and a plunger in a bore of said cylinder housing, said syringe further including a separate tab for extending from an outer surface of said cylinder through an opening in said housing into said bore to engage said plunger and thereby restrict movement of said plunger in said bore, wherein said plunger comprises a circumferential rib which engages said tab when said plunger is rotated to thereby lock said plunger in a longitudinal position.

27. A syringe as in claim 26 wherein said plunger comprises a longitudinal rib and said tab comprises two spaced legs which straddle said longitudinal rib to immediately engage opposite sides thereof, thereby preventing rotation of said plunger while allowing longitudinal movement of said plunger, said longitudinal rib having a notch therein which allows rotation of said plunger when it is at said spaced legs.

28. A syringe including a cylinder housing and a plunger in a bore of said cylinder housing, said syringe further including a separate tab for extending from an outer surface of said cylinder through an opening in said housing into said bore to engage said plunger and thereby restrict movement of said plunger in said bore, wherein said plunger comprises a longitudinal rib and said tab comprises two closely spaced legs which closely straddle said longitudinal rib to immediately engage opposite sides thereof, thereby preventing substantial rotation of said plunger while allowing longitudinal movement of said plunger.

29. A syringe as in claim 28 wherein said longitudinal rib has a notch therein which allows rotation of said plunger when it is at said spaced legs.

* * * * *